(12) United States Patent
Paul

(10) Patent No.: US 6,308,709 B1
(45) Date of Patent: Oct. 30, 2001

(54) ERECTION-FACILITATING CONDOM

(76) Inventor: Robert M. Paul, 2461 Dover Center Rd., Westlake, OH (US) 44145

( * ) Notice: Subject to any disclaimer, the term of this patent is extended or adjusted under 35 U.S.C. 154(b) by 0 days.

(21) Appl. No.: 09/718,331

(22) Filed: Nov. 22, 2000

(51) Int. Cl.[7] ........................................ A61F 6/04
(52) U.S. Cl. ........................ 128/844; 128/918; 600/38
(58) Field of Search ................................. 128/842, 844, 128/918; 604/347–353; 600/38

(56) References Cited

U.S. PATENT DOCUMENTS

| | | |
|---|---|---|
| D. 395,081 | 6/1998 | Bowden . |
| 4,685,913 * | 8/1987 | Austin ................................. 604/353 |
| 5,318,042 | 6/1994 | Gray . |
| 5,327,911 * | 7/1994 | Pien ..................................... 128/844 |
| 5,513,652 | 5/1996 | Schwartz . |
| 5,666,971 | 9/1997 | Anatolievich . |
| 5,741,511 | 4/1998 | Lee et al. . |
| 5,803,085 * | 9/1998 | Asinovsky ........................... 128/844 |
| 5,885,205 | 3/1999 | Kassman . |
| 5,921,914 * | 7/1999 | Tucker ................................... 600/38 |

* cited by examiner

Primary Examiner—Michael A. Brown

(57) ABSTRACT

An erection-facilitating condom for treatment of erection dysfunction. The erection-facilitating condom includes a flexible tubular membrane having a closed end and an open end; and also includes a ring member being attached to the flexible tubular membrane; and further includes a flexible line being connected to the ring member for closing the flexible tubular member tightly about a sex organ of a user.

5 Claims, 2 Drawing Sheets

ERECTION-FACILITATING CONDOM

BACKGROUND OF THE INVENTION

1. Field of the Invention

The present invention relates to a condom and more particularly pertains to a new erection-facilitating condom for treatment of erection dysfunction.

2. Description of the Prior Art

The use of a condom is known in the prior art. More specifically, a condom heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,513,652; 5,318,042; 5,885,205; 5,741,511; 5,666,971; and U.S. pat. No. Des. 395,081.

While these devices fulfill their respective, particular objectives and requirements, the aforementioned patents do not disclose a new erection-facilitating condom. The inventive device includes a flexible tubular membrane having a closed end and an open end; and also includes a ring member being attached to the flexible tubular membrane; and further includes a flexible line being connected to the ring member for closing the flexible tubular member tightly about a sex organ of a user.

In these respects, the erection-facilitating condom according to the present invention substantially departs from the conventional concepts and designs of the prior art, and in so doing provides an apparatus primarily developed for the purpose of treatment of erection dysfunction.

SUMMARY OF THE INVENTION

In view of the foregoing disadvantages inherent in the known types of condom now present in the prior art, the present invention provides a new erection-facilitating condom construction wherein the same can be utilized for treatment of erection dysfunction.

The general purpose of the present invention, which will be described subsequently in greater detail, is to provide a new erection-facilitating condom which has many of the advantages of the condom mentioned heretofore and many novel features that result in a new erection-facilitating condom which is not anticipated, rendered obvious, suggested, or even implied by any of the prior art condom, either alone or in any combination thereof.

To attain this, the present invention generally comprises a flexible tubular membrane having a closed end and an open end; and also includes a ring member being attached to the flexible tubular membrane; and further includes a flexible line being connected to the ring member for closing the flexible tubular member tightly about a sex organ of a user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new erection-facilitating condom which has many of the advantages of the condom mentioned heretofore and many novel features that result in a new erection-facilitating condom which is not anticipated, rendered obvious, suggested, or even implied by any of the prior art condom, either alone or in any combination thereof.

It is another object of the present invention to provide a new erection-facilitating condom which may be easily and efficiently manufactured and marketed.

It is a further object of the present invention to provide a new erection-facilitating condom which is of a durable and reliable construction.

An even further object of the present invention is to provide a new erection-facilitating condom which is susceptible of a low cost of manufacture with regard to both materials and labor, and which accordingly is then susceptible of low prices of sale to the consuming public, thereby making such erection-facilitating condom economically available to the buying public.

Still yet another object of the present invention is to provide a new erection-facilitating condom which provides in the apparatuses and methods of the prior art some of the advantages thereof, while simultaneously overcoming some of the disadvantages normally associated therewith.

Still another object of the present invention is to provide a new erection-facilitating condom for treatment of erection dysfunction.

Yet another object of the present invention is to provide a new erection-facilitating condom which includes a flexible tubular membrane having a closed end and an open end; and also includes a ring member being attached to the flexible tubular membrane; and further includes a flexible line being connected to the ring member for closing the flexible tubular member tightly about a sex organ of a user.

Still yet another object of the present invention is to provide a new erection-facilitating condom that facilitates longer erections by the user.

Even still another object of the present invention is to provide a new erection-facilitating condom that offers protection against pregnancy and the transmission of sexual diseases.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
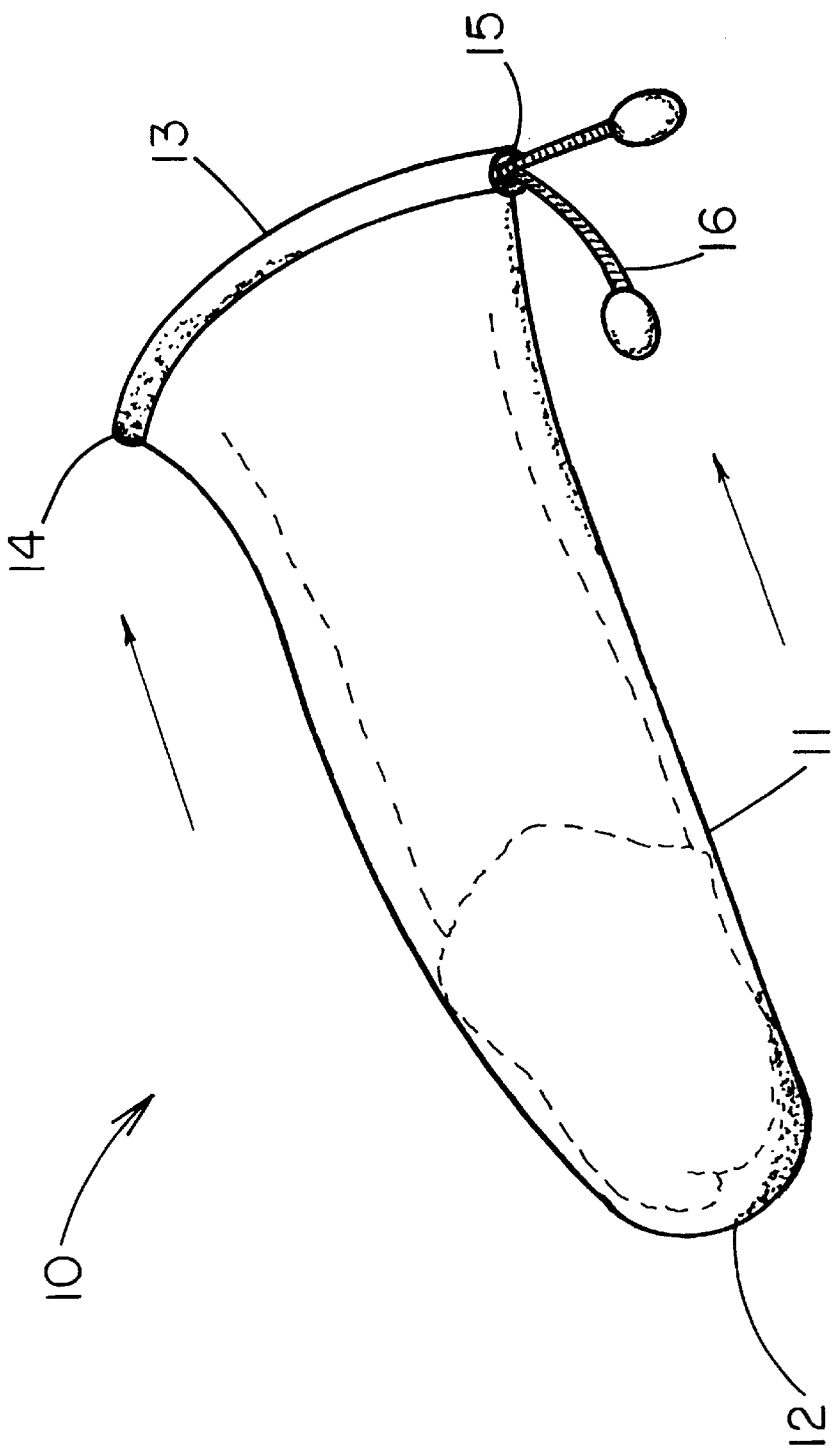
FIG. 1 is a perspective view of a new erection-facilitating condom according to the present invention.
Figure 2:
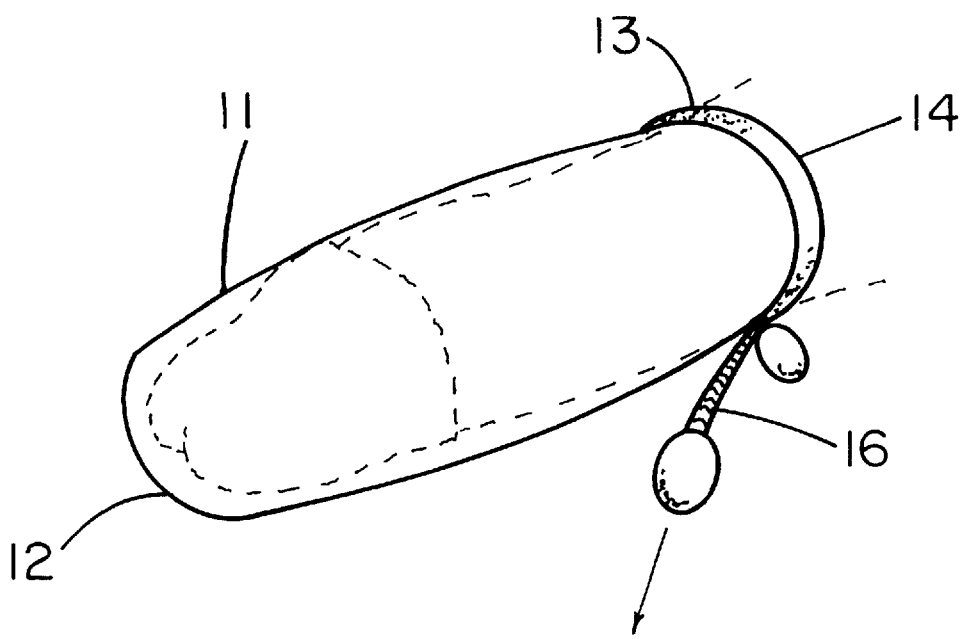
FIG. 2 is another perspective view of the present invention shown in use.
Figure 3:
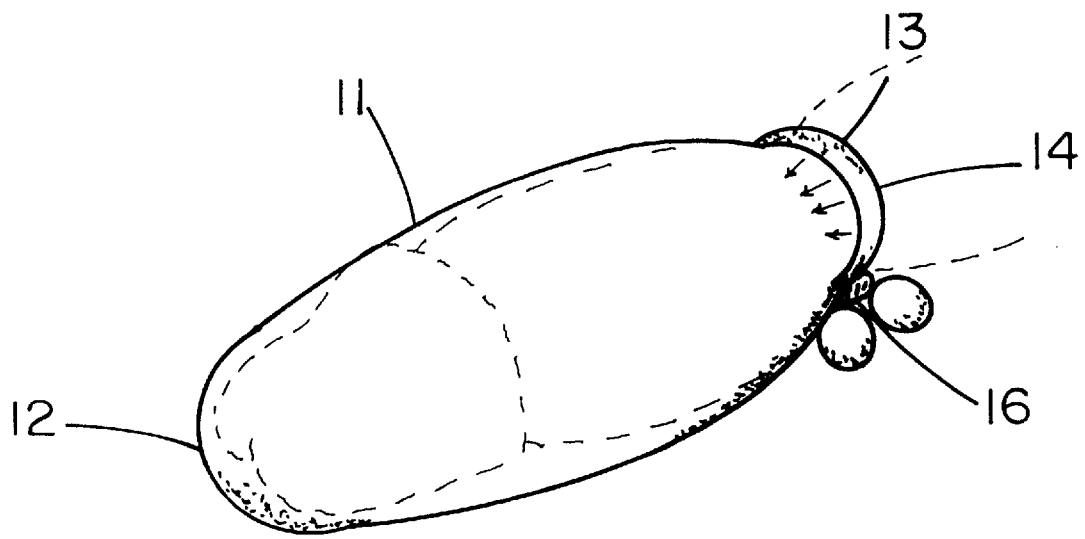
FIG. 3 is a perspective view of the present invention.

With reference now to the drawings, and in particular to FIGS. 1 through 3 thereof, a new erection-facilitating condom embodying the principles and concepts of the present invention and generally designated by the reference numeral 10 will be described.

As best illustrated in FIGS. 1 through 3, the erection-facilitating condom 10 generally comprises a flexible tubular membrane 11 having a closed end 12 and an open end 13. The flexible tubular membrane 11 includes a tubular end 14 extending along an edge of the open end 13 thereof.

A ring member 15 is securely attached to the flexible tubular membrane 11. The ring member 15 is conventionally disposed in the tubular end 14 of the flexible tubular membrane 11 with the ring member 15 being generally made of a rubberized material. A flexible line 16 is conventionally connected to the ring member 15 for closing the flexible tubular member 11 tightly about a sex organ of a user. The flexible line 16 is conventionally disposed in the ring member 15 and is adapted to constrict the open end 13 of the flexible tubular membrane 11 about the sex organ of the user.

In use, the user extends the flexible tubular membrane 11 about one's sex organ pulls on the ends of the flexible line 16 to tighten and constrict the flexible tubular membrane 11 about the base of the sex organ to constrict the flow of blood in the sex organ so that the sex organ will remain erect for longer periods of time.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An erection-facilitating condom comprising:
    a flexible tubular membrane having a closed end and an open end;
    a ring member being attached to said flexible tubular membrane;
    a flexible line being connected to said ring member for closing said flexible tubular member tightly about a penis of a user;
    wherein said flexible line is disposed in said ring, member and is adapted to constrict said open end of said flexible tubular membrane about the penis of the user; and
    said flexible line comprising a pair of ends, each of said ends having a stimulating knob attached thereto.

2. An erection-facilitating condom as described in claim 1, wherein said flexible tubular membrane includes a tubular end extending along an edge of said open end thereof.

3. An erection-facilitating condom as described in claim 2, wherein said ring member is disposed in said tubular end of said flexible tubular membrane.

4. An erection-facilitating condom as described in claim 1, wherein said ring member is generally made of a rubberized material.

5. An erection-facilitating condom comprising:
    a flexible tubular membrane having a closed end and an open end, said flexible tubular membrane including a tubular end extending along an edge of said open end thereof;
    a ring member being attached to said flexible tubular membrane, said ring member being disposed in said tubular end of said flexible tubular membrane, said ring member being generally made of a rubberized material;
    a flexible line being connected to said ring member for closing said flexible tubular member tightly about a penis of a user, said flexible line being disposed in said ring member and being adapted to constrict said open end of said flexible tubular membrane about the penis of the user; and
    said flexible line comprising a pair of ends, each of said ends having a stimulating knob attached thereto.

* * * * *